United States Patent
Loeffler et al.

(10) Patent No.: US 9,700,652 B2
(45) Date of Patent: Jul. 11, 2017

(54) ABSORBABLE MEDICAL IMPLANT MADE OF FIBER-REINFORCED MAGNESIUM OR FIBER-REINFORCED MAGNESIUM ALLOYS

(75) Inventors: Joerg Loeffler, Zürich (CH); Heinz Mueller, Erlangen (DE); Peter Uggowitzer, Ottenbach (CH); Gerhard Kappelt, Uttenreuth (DE)

(73) Assignee: BIOTRONIK VI PATENT AG, Barr (CH)

( * ) Notice: Subject to any disclaimer, the term of this patent is extended or adjusted under 35 U.S.C. 154(b) by 1394 days.

(21) Appl. No.: 11/813,831

(22) PCT Filed: Jan. 18, 2006

(86) PCT No.: PCT/EP2006/000565
§ 371 (c)(1),
(2), (4) Date: Jul. 12, 2007

(87) PCT Pub. No.: WO2006/077154
PCT Pub. Date: Jul. 27, 2006

(65) Prior Publication Data
US 2008/0103594 A1 May 1, 2008

(30) Foreign Application Priority Data

Jan. 20, 2005 (DE) .................. 10 2005 003 188

(51) Int. Cl.
*A61F 2/06* (2013.01)
*A61L 27/42* (2006.01)
*A61L 27/04* (2006.01)

(52) U.S. Cl.
CPC ........... *A61L 27/427* (2013.01); *A61L 27/047* (2013.01)

(58) Field of Classification Search
CPC ............... A61F 2/00; A61F 2250/0014; A61F 2250/0043; A61F 2/82
USPC ................................... 623/1.32, 1.33
See application file for complete search history.

(56) References Cited

U.S. PATENT DOCUMENTS

| 3,687,135 A | 8/1972 | Stroganov et al. |
| 4,279,249 A * | 7/1981 | Vert et al. ................ 606/77 |
| 5,972,027 A * | 10/1999 | Johnson ............ A61F 2/82 |
| | | 424/422 |
| 2001/0002444 A1 * | 5/2001 | Zilla ............... A61F 2/06 |
| | | 623/1.39 |
| 2002/0103526 A1 * | 8/2002 | Steinke ............ A61L 31/10 |
| | | 623/1.11 |
| 2002/0177902 A1 * | 11/2002 | Rioux et al. ......... 623/23.67 |

(Continued)

FOREIGN PATENT DOCUMENTS

| DE | 19731021 | 1/1999 |
| DE | 10115230 | 11/2001 |
| DE | 10118603 | 10/2002 |

(Continued)

*Primary Examiner* — Gregory Anderson
*Assistant Examiner* — Sarah Simpson
(74) *Attorney, Agent, or Firm* — Greer, Burns & Crain, Ltd.

(57) ABSTRACT

A medical implant comprising a composite material which is composed of reinforcement fibers made of a magnesium-containing, bio-corrosive alloy, another bio-corrosive alloy containing a main component that is selected from the group consisting of Mg, Ca, Fe, and Y, or a non-biodegradable fiber material, embedded in a matrix made of crystalline magnesium or magnesium alloys.

24 Claims, 4 Drawing Sheets

(56) References Cited

U.S. PATENT DOCUMENTS

2004/0098090 A1\* 5/2004 Williams et al. ............ 623/1.13
2007/0156231 A1\* 7/2007 Weber .......................... 623/1.38

FOREIGN PATENT DOCUMENTS

| DE | 10128100 | 12/2002 |
|----|----------|---------|
| DE | 10253634 | 5/2004 |
| DE | 10357747 | 1/2005 |
| EP | 0966979 | 12/1999 |
| EP | 1216717 | 6/2002 |
| WO | WO 2004/043474 | 5/2004 |
| WO | WO 2004/110515 | 12/2004 |

\* cited by examiner

ABSORBABLE MEDICAL IMPLANT MADE OF FIBER-REINFORCED MAGNESIUM OR FIBER-REINFORCED MAGNESIUM ALLOYS

PRIORITY CLAIM

This patent application is a U.S. National Phase of copending International Application No. PCT/EP2006/000565, filed Jan. 18, 2006, which claims priority to German Patent Application No. 10 2005 003 188.9, filed Jan. 20, 2005, the disclosures of which are incorporated herein by reference in their entirety.

FIELD OF THE INVENTION

The present invention relates to an absorbable medical implant comprising a composite material comprising a crystalline matrix made of biocorrodible magnesium or magnesium alloys which is reinforced using amorphous or nanocrystalline fibers made of a magnesium-containing biocorrodible alloy, another biocorrodible alloy, or a fiber material which is not biologically degradable.

BACKGROUND OF THE INVENTION

Medical implants for greatly varying uses are known in the art. A shared goal in the implementation of modern medical implants is high biocompatibility, i.e., a high degree of tissue compatibility of the medical product inserted into the body. Frequently, only a temporary presence of the implant in the body is necessary to fulfill the medical purpose. Implants made of materials which do not degrade in the body are to be removed again, because rejection reactions of the body may occur in the medium and long term even with highly biocompatible permanent materials.

One approach for solving the above-mentioned set of problems is to mold the implant entirely or in part from a biocorrodible material. Biocorrosion is defined in the present disclosure as microbial procedures or processes solely caused by the presence of bodily media, which result in a gradual degradation of the structure comprising the material. At a specific time, the implant, or at least the part of the implant which comprises the biocorrodible material, loses its mechanical integrity. The degradation products are resorbed by the body, small residues being tolerable.

Biocorrodible materials have been developed, inter alia, on the basis of polymers of synthetic nature or natural origin. Because of the material properties, but particularly also because of the degradation products of the synthetic polymers, the use of biodegradable polymers is still significantly limited. Thus, for example, orthopedic implants must frequently withstand high mechanical strains and vascular implants, e.g., stents, must meet very special requirements for modulus of elasticity, brittleness, and moldability depending on their design.

One promising attempted achievement provides the use of biocorrodible metal alloys for this purpose. Thus, it is suggested in German Patent Application No. 197 31 021 A1 that medical implants be molded from a metallic material whose main component is to be selected from the group of alkali metals, alkaline earth metals, iron, zinc, and aluminum. Alloys based on magnesium, iron, and zinc are described as especially suitable. Secondary components of the alloys may be manganese, cobalt, nickel, chromium, copper, cadmium, lead, tin, thorium, zirconium, silver, gold, palladium, platinum, silicon, calcium, lithium, aluminum, zinc, and iron. Furthermore, the use of a biocorrodible magnesium alloy having a proportion of magnesium greater than 90%, yttrium 3.7-5.5%, rare earth metals 1.5-4.4%, and the remainder less than 1% is known from German Patent Application No. 102 53 634 A1, which is suitable, in particular, for producing an endoprosthesis, e.g., in the form of a self-expanding or balloon-expandable stent. Notwithstanding the progress achieved in the field of biocorrodible metal alloys, the alloys known up to this point are also only capable of restricted use because of their material properties, such as strength and corrosion behavior. In particular, the relatively rapid biocorrosion of magnesium alloys and their low strength in comparison to other metallic materials causes a limitation of the field of use. A medical implant is described as an innovative approach in German Patent Application No. 10 2005 003 188.9, which comprises or contains a biocorrodible amorphous or nanocrystalline alloy. The construction of implants made of magnesium and magnesium alloys, which have an increased strength in comparison to crystalline magnesium and magnesium alloys, is thus possible. However, this advantage is typically acquired by a loss of deformability and stability under alternating load because of increased bending rigidity. This in turn greatly restricts the field of use of these alloys.

SUMMARY OF THE DISCLOSURE

The present invention provides a material which has comparably high biocompatibility to the known biocorrodible magnesium alloys, in particular, and provides improved material properties for use in implants. If possible, the field of use of biocorrodible metal alloys in implants is to be expanded.

A feature of the present invention is achieved by the medical implant having a biocorrodible alloy composite material, which is reinforced using amorphous or nanocrystalline fibers made of a magnesium-containing, biocorrodible alloy, another biocorrodible alloy, or a fiber material which is not biologically degradable, made of magnesium or a magnesium alloy having a main component of the amorphous or nanocrystalline fibers selected from the group consisting of Mg, Ca, Fe, and Y.

The present invention produces medical implants from crystalline magnesium or magnesium alloys in a targeted way depending on the mechanical strain having reinforcement fibers made of a biocorrodible, amorphous, or nanocrystalline alloy having a main component entirely or partially selected from the group consisting of Mg, Ca, Fe, and Y. The amorphous or nanocrystalline alloys are distinguished in relation to the known crystalline metal alloys by their typically increased strength and a delayed in vivo corrosion behavior. A composite material having completely novel mechanical properties results by embedding amorphous or nanocrystalline fibers in a crystalline matrix, which is thus more easily deformable. The amorphous or nanocrystalline fibers are supported over their entire area by the crystalline matrix. Significantly higher elasticity in comparison to an implant which is exclusively manufactured from amorphous or nanocrystalline alloys or contains larger coherent volume proportions of these alloys results for the implant of the present invention. Simultaneously, the increase of strength caused by the amorphous and nanocrystalline structure of the fibers is largely maintained, or is even exceeded, by the composite material thus resulting due to the additional supporting effect on the fibers. The fibers may additionally have their shape tailored optimally to the mechanical strains of the component.

According to the present disclosure, the main components of an alloy are the alloy components whose weight proportion in the alloy is highest. In the preferred alloy compositions described in greater detail hereinbelow, all further proportions of the alloy components are always predefined in such a way that Mg, Ca, Fe, or Y has the highest weight proportion.

For purposes of the present disclosure, amorphous alloys do not form a crystal structure and the material remains in a type of configuration without periodicity, without long-range order, similar to the atoms in a melt, but having fixed atomic positions. Amorphous alloys are also referred to as metallic glasses (glassy metals, amorphous metals). Even if the alloys are referred to as amorphous, the alloys still always have a pronounced short-range order both topologically and also chemically, which is frequently similar to that of the corresponding crystalline equilibrium phase.

Nanocrystalline alloys are not entirely amorphous, but rather contain individual crystals whose size is defined in the present case as less than or equal to 100 nm. Nanocrystalline alloys are also distinguished by chemical and topological properties deviating from the crystalline equilibrium phase.

Various production methods known in the prior art may be used to prevent a crystal structure from forming and to keep the material in the amorphous or nanocrystalline state. Bulk molded semifinished and finished products made of amorphous or nanocrystalline alloys (also called bulk metallic glasses (BMG)) may be produced, for example, by rapid quenching of a melt or a vapor. In so-called melt spinning, the liquid metal is guided onto a rapidly rotating, cooled cylinder. So-called levitation melting is still in the development phase. For purposes of the present disclosure, a preform made of the individual alloy elements is melted in the floating state in vacuum. A fiber may be drawn from these floating melt droplets using continuous removal at uniform withdrawal speed.

Material properties and production methods for magnesium-containing amorphous alloys are described by (i) A. Inoue and T. Masumoto, Material Science and Engineering, A173 (1993) pp. 1 to 8; (ii) G. Yuan, T. Zhang, and A. Inoue, Materials Transactions, Vol. 44, No. 11 (2003) pp. 2271 to 2275, and (iii) W. M. Rainforth and H. Jones, Scripta Materialia, Vol. 37, No. 3 (1997) pp. 311 to 314.

Theoretically, any alloy may be obtained in amorphous or nanocrystalline modification by suitable method control. Alloys which are especially suitable in practice and for the purpose of the present disclosure are distinguished by a favorable ratio of glass transition temperature $T_g$ and temperature of the melt $T_1$ (as a result of the known Turnbull criterion; see, D. Turnbull, Metall Trans B (1981) 271). Furthermore, it is known that the addition of alloy components may result in the formation of eutectic phases in the melts and reinforced chemical and topological differences between the individual alloy components, e.g., in atomic size and in binding behavior, may prevent crystal formation during the cooling of the melt.

Data collections of phase diagrams of binary or ternary alloys may be used to find suitable alloy systems (Massalski T. B., Okamoto H., Subramanian P. R., Kacprizak L., Binary alloy phase diagrams, vols. 1 to 3, Materials Park (OH): ASM International, 1990/1; Villars P., Prince A., Okamoto H., Handbook of ternary alloy phase diagrams, vols. 1 to 10, Materials Park (OH): ASM International, 1995). In a further approach, melts having the alloy components coming into consideration are slowly cooled in the presence of high gravimetric forces. This may be achieved by providing the melts in crucibles which are accommodated on a centrifuge and slowly lowering the temperature during the centrifuging (Löffler J. F., Johnson W. L., Intermetallics 10 (2002), pp. 1167 to 1175; Löffler J. F., Intermetallics 11 (2003), pp. 529 to 540; Löffler J. F., Peker A., Bossuyt S., Johnson W. L., Materials Science and Engineering A 375-377 (2004) pp. 341 to 345). Accordingly, it is possible without further measures for one skilled in the art having access to the literature values or the cited gravimetric assay methods to identify eutectic materials or compositions similar to the eutectic materials, which may form especially stable amorphous or nanocrystalline alloys.

The amorphous or nanocrystalline alloys are to be selected in their composition in such a way that they are biocorrodible. For purposes of the present disclosure, alloys are referred to as biocorrodible in which degradation occurs in a physiological environment, which finally results in the entire implant or the part of the implant formed by the material losing its mechanical integrity. Artificial plasma, as has been previously described according to EN ISO 10993-15:2000 for biocorrosion assays (composition NaCl 6.8 g/l. $CaCl_2$ 0.2 g/l. KCl 0.4 g/l. $MgSO_4$ 0.1 g/l. $NaHCO_3$ 2.2 g/l. $Na_2HPO_4$ 0.126 g/l. $NaH_2PO_4$ 0.026 g/l), is used as a testing medium for testing the corrosion behavior of an alloy coming into consideration. For this purpose, a sample of the alloy to be assayed is stored in a closed sample container with a defined quantity of the testing medium at 37° C. At time intervals—tailored to the corrosion behavior to be expected—of a few hours up to multiple months, the sample is removed and examined for corrosion traces in a known way.

Vascular implants in the form of stents are preferably to be designed in regard to the biocorrodible amorphous or nanocrystalline alloys used for the reinforcement fibers in such a way that a mechanical integrity of the implant is maintained for 2-20 weeks. Implants as an occluder are to be designed in regard to the biocorrodible amorphous or nanocrystalline alloys for the reinforcement fibers in such a way that the mechanical integrity of the implant is maintained for 6-12 months. Orthopedic implants for osteosynthesis are to be designed in regard to the biocorrodible amorphous alloy composition for the reinforcement fibers in such a way that the mechanical integrity of the implant is maintained for 6-36 months.

The following are especially preferable:
(a) An alloy of the composition of the formula MgZnX, in which (i) a proportion of Zn in the alloy is 10-40 weight-percent and (ii) X stands for one or more elements selected from the group consisting of Ln, Y, Si, Al, and Ca and a proportion of X in the alloy is 0-20 weight-percent.
(b) An alloy of the composition MgZn, having a proportion of Zn in the alloy of 26-32 weight-percent, in particular approximately 28.1 weight-percent.
(c) An alloy of the composition MgZnLn, in which a proportion of Zn in the alloy is 10-40 weight-percent and a proportion of Ln in the alloy is 1-12 weight-percent.
(d) An alloy of the composition MgZnY, in which a proportion of Zn in the alloy is 10-40 weight-percent and a proportion of Y in the alloy is 1-12 weight-percent.
(e) An alloy of the composition MgZnY, in which a proportion of Zn in the alloy is 13-17 weight-percent and a proportion of Y in the alloy is 8-12 weight-percent.
(f) An alloy of the composition MgZnY, in which a proportion of Zn in the alloy is approximately 15 weight-percent and a proportion of Y in the alloy is approximately 10 weight-percent.

(g) An alloy of the composition MgZnSi, in which a proportion of Si in the alloy is 0.01-2 weight-percent and a proportion of Zn in the alloy is 10-40 weight-percent.

(h) An alloy of the composition MgZnAl, in which a proportion of Al in the alloy is 0.01-20 weight-percent and a proportion of Zn in the alloy is 10-40 weight-percent.

(i) An alloy of the composition MgZnCa, in which a proportion of Ca in the alloy is 0.01-20 weight-percent and a proportion of Zn in the alloy is 10-40 weight-percent.

(j) An alloy of the composition MgY, in which a proportion of Y in the alloy is 1-30 weight-percent.

(k) An alloy of the composition MgY, in which a proportion of Y in the alloy is 7-11 weight-percent.

(l) An alloy of the composition MgY, in which a proportion of Y in the alloy is approximately 8.9 weight-percent.

(m) An alloy of the composition MgYLn, in which a proportion of Y in the alloy is 1-30 weight-percent and a proportion of Ln in the alloy is 1-12 weight-percent.

(n) An alloy of the composition MgCaAl, in which a proportion of Ca in the alloy is 0.01-20 weight-percent and a proportion of Al in the alloy is 0.01-20 weight-percent.

(o) An alloy of the composition MgCaSi, in which a proportion of Ca in the alloy is 0.01-20 weight-percent and a proportion of Si in the alloy is 0.01-2 weight-percent.

The alloys described hereinabove in paragraphs (a)-(o) appear, according to initial experimental attempts, to meet the requirements for the material composition of medical implants, in particular biocompatibility.

The collective term "lanthanides" is understood in the present case as the 14 elements following lanthanum, namely cerium (58), praseodymium (59), neodymium (60), promethium (61), samarium (62), europium (63), gadolinium (64), terbium (65), dysprosium (66), holmium (67), erbium (68), thulium (69), ytterbium (70), and lutetium (71). The symbol Ln is used for the lanthanides.

The medical implants according to the present disclosure preferably contain fibers or wires made of the alloy, because they may be manufactured and processed easily and the danger of crystallization is kept low. The wires are fibers preferably having a diameter in the range from 50-300 µm and may also be woven to form woven fabrics or mats. The semifinished product thus obtained is embedded in a further step in a matrix made of crystalline magnesium or a crystalline magnesium alloy. The composite material thus arising displays a significantly altered mechanical behavior with slightly changed corrosion kinetics in comparison to the two individual components. If necessary, the degradation kinetics may also be influenced for this purpose by setting a potential difference in a targeted way between fiber and matrix by the selection of fiber and matrix materials.

If the implant is a vascular implant in the form of a stent, the main framework of the stent is preferably molded from the fibers or wires of the alloy and this framework is then encased in a matrix made of crystalline magnesium or a crystalline magnesium alloy or embedded in a sintering process. In particular, balloon-expandable stent designs may be implemented by the use of fibers and wires.

Furthermore, the implant may contain a sintered body which is manufactured from a powder of one of the two alloys. By adding suitable pore formation agents, which are known per se in the prior art, a porosity of the material may be predefined. A porous material suggests itself, in particular, as an active ingredient depot, the active ingredient accommodated in the pores being released during the biocorrosion of the alloy in the body or gradually diffusing out of the pores. It is also conceivable to alter a surface of the medical implant in the area of the alloy by microstructuring in such a way that adhesion of active ingredients or the coating material absorbing the active ingredient is made easier.

According to a further preferred exemplary embodiment, the medical implant is implemented as an orthopedic implant, in particular, for osteosynthesis. Thus, biocorrodible orthopedic implant suggests themselves in particular in oral, mandibular, and facial surgery, hand surgery, and as fixation implants and nails for fractures. One advantage in comparison to permanent implants is that, in contrast to the permanent implant, a renewed operative intervention is not necessary for removal and the composite materials having amorphous or nanocrystalline reinforcement fibers have better material properties in comparison to crystalline materials of identical composition. In relation to the known biocorrodible metallic implants, higher strength and altered corrosion kinetics, either delayed or accelerated, depending on the application, are to be expected for such a composite material. In addition, the alloy range for the fibers made of amorphous or nanocrystalline alloys may be varied in a wider range than comparable crystalline alloys and thus meet requirements for biocompatibility better, for example.

In a further preferred exemplary embodiment, the implant is implemented to treat vulnerable plaque. These arterial deposits are responsible for a majority of myocardial infarctions, often with lethal outcome, although the reduction of the vessel diameter is often only slight. An implant similar in its design to a stent which is known per se may be placed in the area of vulnerable plaque according to this indication. It has been shown that, in particular, magnesium alloys exert a positive physiological effect on vulnerable plaque during the alloy's degradation in the body and thus a prophylactic treatment of the plaque is possible. In particular, the implants suitable for this purpose also act as carriers of active ingredients, using which the inflammatory processes during the formation of vulnerable plaque may be counteracted. The increased mechanical carrying capacity of a composite material made of crystalline matrix and amorphous or nanocrystalline fibers results in a secure enclosure of the vulnerable plaque on the vascular wall over the entire duration of treatment in this case.

A further preferred possible use of medical implants having the composite material according to the present disclosure is in pediatrics. In particular, in vascular use, the treatment of vessels using permanent implants is not possible due to growth or these implants have to be removed operatively later. The clinical advantage in comparison to current treatment methods using permanent implants is obvious.

The present disclosure is explained in greater detail on the basis of exemplary embodiments and the associated drawings.

BRIEF DESCRIPTION OF THE DRAWINGS

FIG. 2b shows a partial detail view of a vascular implant in the form of a balloon-expandable stent of FIG. 2a;

FIG. 3b shows a side elevation view of the vascular implant and fiber mat of FIG. 3a.

DETAILED DESCRIPTION OF THE EMBODIMENTS

Figure 1:
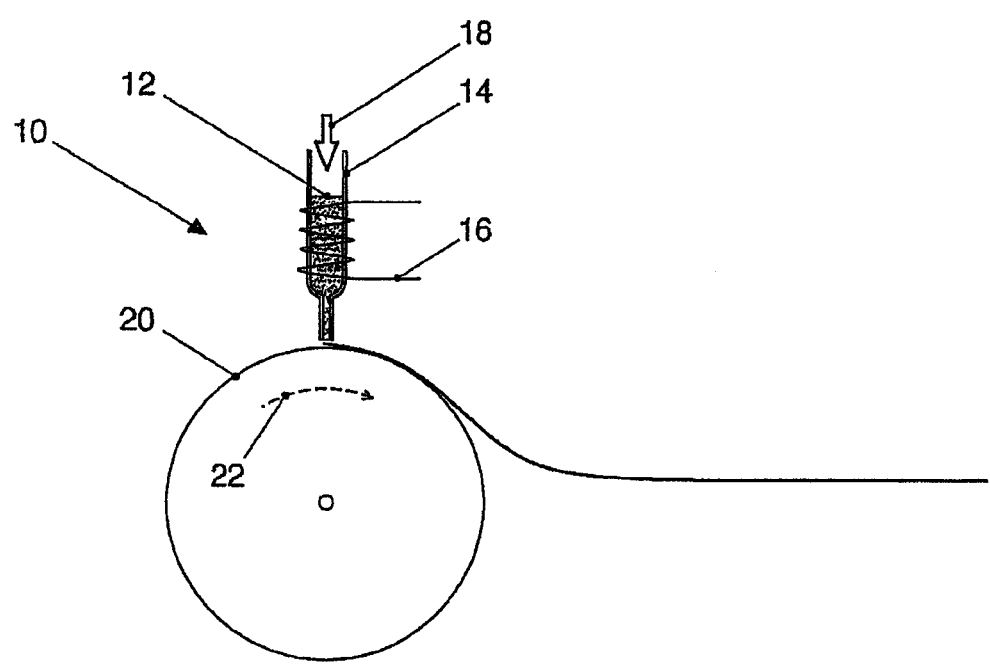
FIG. 1 shows a schematic illustration of the principle of a melt spinner for producing amorphous alloys.

FIG. 1 shows, in very schematic form, the mode of operation of a melt spinner 10 for producing rapidly solidified amorphous alloys. A melt 12 is provided in a sample container 14, which is heatable using a heater 16. Due to the application of pressure (shown by the arrow 18), the melt 12 exits from a hole at the lower end of the sample container 14 and falls on a rapidly rotating, cooled cylinder 20 made of copper (a rotation direction of the cylinder 20 is indicated by the arrow 22). As a result of the very rapid cooling of the material, a transition into the crystalline state may be prevented. Criteria for glass formation are particularly (i) low eutectics, because a low stability of the crystal and/or a higher stability of the melt is to be expected there and (ii) a significant size difference of the participating atoms of the alloy.

For the preparation of amorphous or nanocrystalline alloys of especially suitable compositions, either binary and ternary alloy systems may be taken from the relevant data collections or may be determined experimentally in a standard way by gravimetric assays of cooling melts in heatable centrifuges. Thus, for example, it is known that the binary alloy MgZn has a eutectic at 71.9 weight-percent magnesium and 28.1 weight-percent zinc. MgZn alloys of this composition or a composition near the eutectic may be produced especially easily as amorphous or nanocrystalline alloys. However, it is to be emphasized that, for many medical technology applications, the amorphous alloy system which is most thermodynamically stable is not necessarily to be selected, but rather the corrosion behavior and, of course, the biocompatibility are influencing factors for the selection of the alloy. The mechanical and thermal strains arising during the production of the medical implants are typically so low that crystallizing out of the alloys may be largely avoided.

Figure 2A:
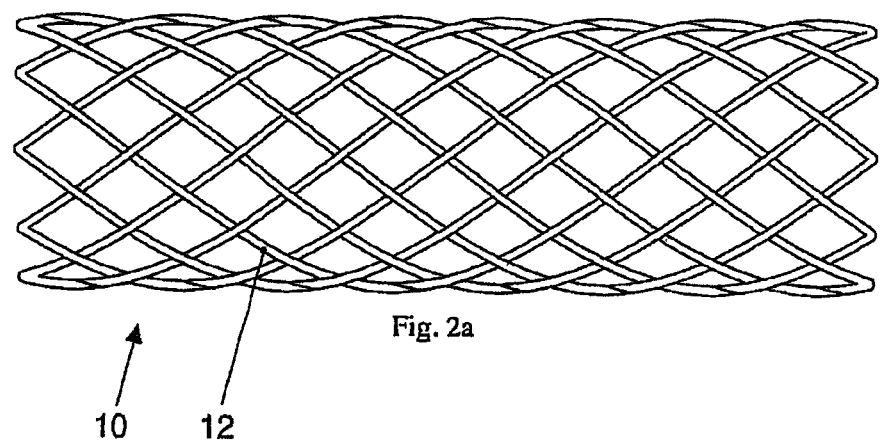
FIG. 2a shows a top view of a vascular implant in the form of a balloon-expandable stent.
Figure 2B:
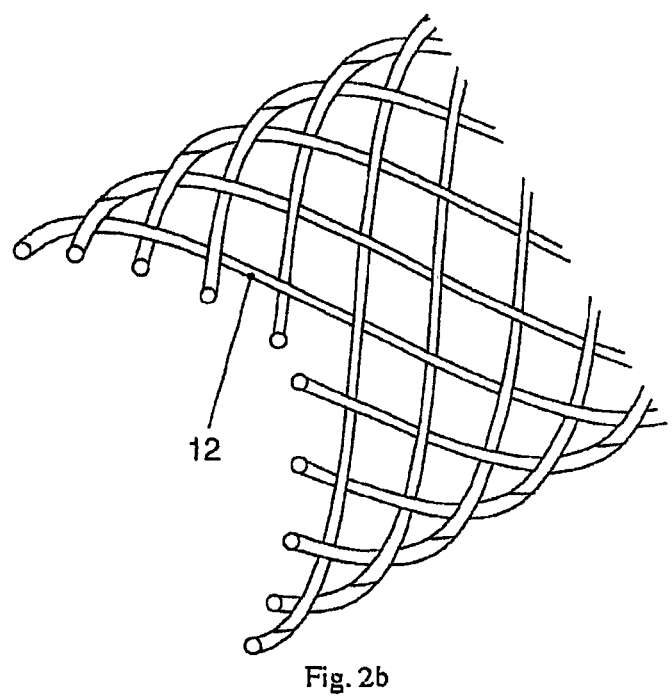

FIG. 2a schematically shows a vascular implant in the form of a balloon-expandable stent 10 and FIG. 2b shows an enlarged partial detail thereof. The stent 10 is formed by a mesh-like woven wire braid having peripheral wire sections 12 in a spiral. The stent design only has subordinate significance in the present disclosure and is thus used for illustration. The stent design illustrated in FIGS. 2a and 2b is laid out as balloon-expandable, i.e., the stent design may be mechanically transferred starting from a compressed first state into an expanded second state. Structures of this type are well-known in the prior art. For the implementation, the material used must meet specific criteria such as modulus of elasticity, brittleness, and strength. This may be achieved by reinforcing the webs 12 of the stent 10 using embedded fibers made of a biocorrodible amorphous or nanocrystalline magnesium alloy. The webs 12 have a wall thickness in the range from 50-300 μm.

Figure 3A:
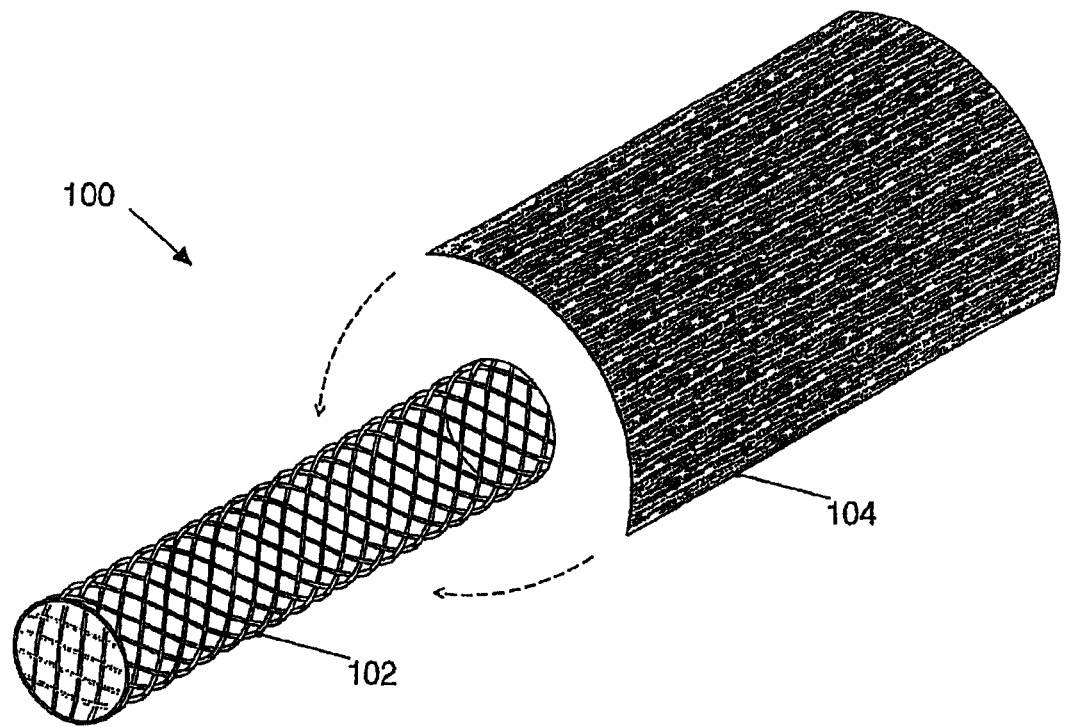
FIG. 3a shows a schematic view of a vascular implant having a fiber mat made of an amorphous alloy.
Figure 3B:
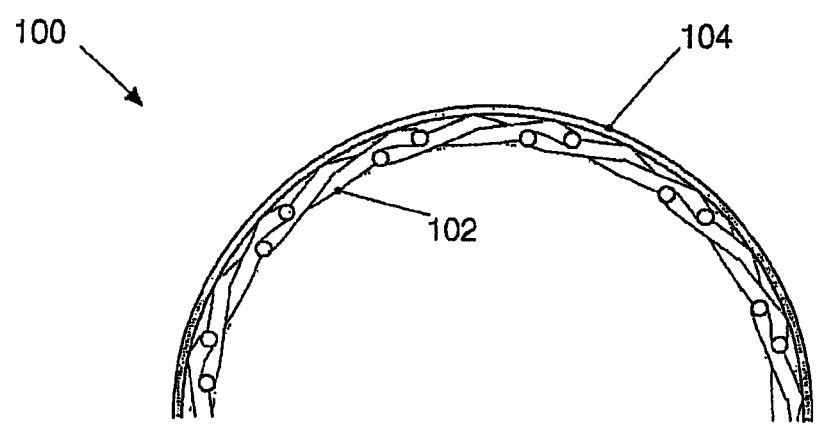

FIGS. 3a and 3b show a further vascular implant in which biocorrodible amorphous alloys are used. The vascular implant is implemented as a so-called graft stent 100 and comprises a stent-like main framework 102 and a stretchable envelope 104 which receives the main framework 102. The main framework 102 may be designed in the way described in FIGS. 2a and 2b, i.e., the main framework may comprise a biocorrodible amorphous alloy. However, a more permanent material, such as medical steel, is also conceivable. The envelope 104 comprises thin fibers of a biocorrodible amorphous magnesium alloy which are woven together. The alloy compositions of main framework 102 and envelope 104 may deviate from one another. The envelope 104 is designed in such a way that the envelope 104 is stretchable upon expansion of the main framework 102 and allows temporary coverage or even sealing of the vascular wall, e.g., after vascular rupture. FIG. 3b shows a half cross-section through the graft stent 100, which is to illustrate the relative position of the main framework 102 to the envelope 104.

Figure 4:
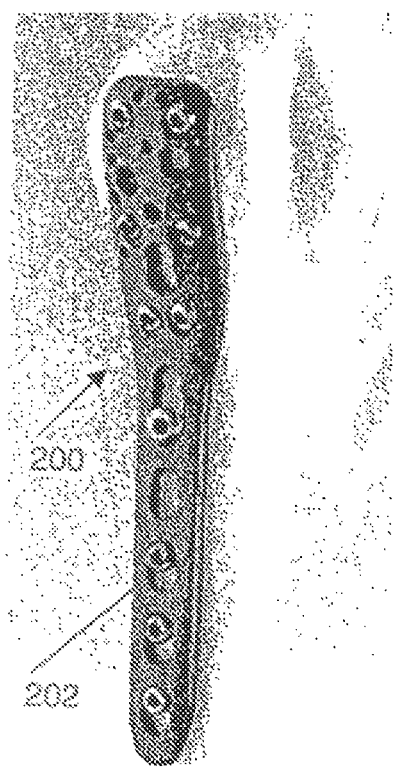
FIG. 4 shows an orthopedic implant for osteosynthesis of fragment fractures.

FIG. 4 shows an orthopedic implant for the osteosynthesis of fragment fractures in the area of an upper arm bone. The implant 200 has a geometry tailored to the medical function and has multiple openings through which screws 202 for fixation of the implant 200 on the bone to be fixed are guided. The implant 200 is molded from a biocorrodible composite material, which is reinforced using amorphous or nanocrystalline fibers made of magnesium or a magnesium alloy, which is to be designed in such a way that the implant may absorb the mechanical strains and loses its mechanical integrity at earliest after approximately 12 months because of the advancing biocorrosion, because it must fulfill its medical function up to this time. The screws 202 are also molded from a biocorrodible composite material, which is reinforced using amorphous or nanocrystalline fibers made of magnesium or a magnesium alloy, which displays the same corrosion behavior as the implant 200, but does not necessarily have to comprise the same alloy composition as the implant 200, because other requirements exist for its strength. For the intended purpose of the implant 200 and the screws 202, biocorrodible composite materials of high strength which are reinforced using amorphous or nanocrystalline fibers are preferred.

All patents, patent applications and publications referred to herein are incorporated by reference in their entirety.

What is claimed is:

1. A medical implant, comprising: a biocorrodible alloy composite material comprising a matrix of crystalline magnesium or crystalline magnesium alloy which is reinforced using amorphous or nanocrystalline fibers made of a magnesium-containing, biocorrodible metal alloy, the amorphous or nanocrystalline fibers being embedded in the matrix of crystalline magnesium or crystalline magnesium alloy, wherein the implant is deformable, wherein the amorphous or nanocrystalline reinforcement fibers have a composition MgZnX, wherein (i) a proportion of Zn in the alloy is 10-40 weight-percent and (ii) X stands for one or more elements selected from the group consisting of Ln, Y, Si, Al, and Ca, and wherein a proportion of X in the alloy is 0-20 weight-percent.

2. The implant of claim 1, wherein the amorphous or nanocrystalline reinforcement fibers have the composition MgZn, wherein a proportion of Zn in the alloy is from 26 to 32 weight-percent.

3. The implant of claim 2, wherein the proportion of Zn in the alloy is 28.1 weight-percent.

4. The implant of claim 1, wherein the amorphous or nanocrystalline reinforcement fibers have the composition MgZnLn, wherein a proportion of Ln in the alloy is from 1 to 12 weight-percent.

5. The implant of claim 1, wherein the amorphous or nanocrystalline reinforcement fibers have the composition MgZnY, wherein a proportion of Y in the alloy is from 1 to 12 weight-percent.

6. The implant of claim 5, wherein a proportion of Zn in the alloy is from 13 to 17 weight-percent and a proportion of Y in the alloy is from 8 to 12 weight-percent.

7. The implant of claim 6, wherein a proportion of Zn in the alloy is approximately 15 weight-percent and a proportion of Y in the alloy is approximately 10 weight-percent.

8. The implant of claim 1, wherein the amorphous or nanocrystalline reinforcement fibers have the composition MgZnSi, wherein a proportion of Si in the alloy is from 0.01 to 2 weight-percent.

9. The implant of claim 1, wherein the amorphous or nanocrystalline reinforcement fibers have the composition MgZnAl, wherein a proportion of Al in the alloy is from 0.01 to 20 weight-percent.

10. The implant of claim 1, wherein the amorphous or nanocrystalline reinforcement fibers have the composition MgZnCa, wherein a proportion of Ca in the alloy is from 0.01 to 20 weight-percent.

11. The implant of claim 1, wherein the amorphous or nanocrystalline reinforcement fibers are woven as a woven fabric or mats.

12. The implant of claim 1, wherein the amorphous or nanocrystalline reinforcement fibers have a diameter in the range of from 50 to 300 μm.

13. The implant of claim 1, wherein the implant has an at least regionally porous surface.

14. The implant of claim 1, wherein the implant comprises a vascular implant.

15. The implant of claim 14, wherein the vascular implant comprises a stent and a main framework of the stent comprises fibers of the magnesium-containing biocorrodible metal alloy, wherein the fibers are woven as a woven fabric or mats.

16. The implant of claim 15, wherein the stent is self-expanding.

17. The implant of claim 1, wherein the implant is an orthopedic implant.

18. The implant of claim 1, wherein the implant fixes tissue in the vascular system.

19. The implant of claim 1, wherein the implant is an implant for use in pediatrics.

20. The implant of claim 1, wherein the implant is an implant for treating vulnerable plaque.

21. The implant of claim 1, wherein the amorphous or nanocrystalline fibers are supported over their entire area by the matrix of crystalline magnesium or crystalline magnesium alloy.

22. A medical implant, comprising: a biocorrodible alloy composite material comprising a matrix of crystalline magnesium or crystalline magnesium alloy which is reinforced using amorphous or nanocrystalline fibers made of a magnesium-containing, biocorrodible metal alloy, or another biocorrodible metal alloy, the amorphous or nanocrystalline fibers being embedded in the matrix of crystalline magnesium or crystalline magnesium alloy, a main component of the magnesium-containing, biocorrodible metal alloy, or the another biocorrodible metal alloy being selected from the group consisting of Mg, Ca, Fe, and Y, wherein the implant is deformable; and wherein the amorphous or nanocrystalline reinforcement fibers have the composition:

MgY, wherein a proportion of Y in the alloy is from 1 to 30 weight-percent; or

MgYLn, wherein a proportion of Y in the alloy is from 1 to 30 weight-percent and a proportion of Ln in the alloy is from 1 to 12 weight-percent; or MgCaAl, wherein a proportion of Ca in the alloy is from 0.01 to 20 weight-percent and a proportion of Al in the alloy is from 0.01 to 20 weight-percent; or MgCaSi, wherein a proportion of Ca in the alloy is from 0.01 to 20 weight-percent and a proportion of Si in the alloy is from 0.01 to 2 weight-percent.

23. The implant of claim 22, wherein the amorphous or nanocrystalline reinforcement fibers have the composition MgY, and wherein a proportion of Y in the alloy is from 7 to 11 weight-percent.

24. The implant of claim 22, wherein the amorphous or nanocrystalline reinforcement fibers have the composition MgY, and wherein the proportion of Y in the alloy is 8.9 weight-percent.

* * * * *